US005866155A

United States Patent [19]
Laurencin et al.

[11] Patent Number: 5,866,155
[45] Date of Patent: Feb. 2, 1999

[54] METHODS FOR USING MICROSPHERE POLYMERS IN BONE REPLACEMENT MATRICES AND COMPOSITION PRODUCED THEREBY

[75] Inventors: Cato Laurencin, Elkins Park; Mark Borden, Phoenixville, both of Pa.

[73] Assignee: Allegheny Health, Education and Research Foundation, Philadelphia, Pa.

[21] Appl. No.: 749,772

[22] Filed: Nov. 20, 1996

[51] Int. Cl.⁶ .............................. A61F 2/28; A61K 9/50; B01J 13/02; B32B 5/16

[52] U.S. Cl. ........................ 424/425; 424/501; 424/502; 264/4.1; 264/4.3; 264/4.33; 264/4.6; 428/402.21

[58] Field of Search .................................. 424/425, 422, 424/501, 502; 264/4.1, 4.3, 4.33, 4.6; 428/402.21

[56] References Cited

U.S. PATENT DOCUMENTS

| | | | |
|---|---|---|---|
| 4,851,228 | 7/1989 | Zentner et al. | 424/456 |
| 5,120,340 | 6/1992 | Ducheyne et al. | 65/18.3 |
| 5,518,680 | 5/1996 | Cima et al. | 264/401 |
| 5,626,861 | 5/1997 | Laurencin et al. | 424/426 |

OTHER PUBLICATIONS

Attawia et al., "Immunofluorescence and confocal laser scanning microscopy studies of osteoblast growth and phenotype expression in three–dimensional degradable synthetic matrices", *J. Biomed. Mater. Res.* 1995 29:843–848.
Attawia et al., "Osteoblast–like Cell Adherence and Migration Through 3–Dimensional Porous Polymer Matrices", *Biochem. and Biophys. Res. Commun.* 1995 213:639–644.
Chow, L.C., "Development of Self–Setting Calcium Phosphate Cements", *Centen. Mem. Issue Ceramic Soc. Jpn* 1991 99:954.
Chow et al., "Self–Setting Calcium Phosphate Cements", *Mater. Res. Soc. Symp. Proc.* 1993 179:3–24.
Coombes, A.D. and Heckman, J.D., "Gel casting of resorbable polymers", *Biomaterials* 1992 13:217–224.
Cornell, C.N., "Initial clinical experience with use of Collagraft™ as a bone graft substitute", *Tech. Orthop.* 1992 7:55.

Devin et al., "Three–dimensional degradable porous polymer–ceramic matrices for use in bone repair", *J. Biomateri. Sci. Polymer Edn.* 1996 7:661–669.
Feenstra, L. and De Groot, K. "Medical use of calcium phosphate ceramics", *Bioceramics of Calcium Phosphate*, De Groot, K. Ed., CRC Press, Boca Raton, Florida, 1983, pp. 131–141.
Feldman, D. and Esteridge, T. *Transactions 2nd World Congress Biomaterials Society*, 10th Annual Meeting, 1984, p. 37.
Hulbert et al., "Potential of Ceramic Materials as Permanently Implantable Skeletal Prosthese", *J. Biomed. Mat. Res.* 1970 4:443.
Keaveney, T.M. and Hayes, W.C. "Mechanical Properties of Cortical and Trabecular Bone." In *Bone vol. 7: Bone Growth–B*, B.K. Hall Ed., CRC Press, Boca Raton, 1992, pp. 285–344.
Levin et al., "A Comparison of Illiac Marrow and Biodegradable Ceramic in Periodontal Defects", *J. Biomed. Mat. Res.* 1975 9:183.
Mikos et al., "Preparation and characterization of poly(L–lactic acid) foams", *Polymer* 1994 35:1068–1077.
Mirtchi et al., "Calcium phosphate cements: study of the β–tricalcium phosphate monocalcium phosphate system", *Biomaterials* 1989 10:475.
Nery et al., "Bioceramic Implants in Surgically Produced Infrabony Defects", *J. Periodotol.* 175 46:328.
Odian, G., *Principle of Polymerization*, John Wiley and Sons, New York, 1991, pp. 29–33.
Robinson et al., "Calvarial bone repair with porous D,L–polylactide", *Otolaryngol. Head and Neck Surg.* 1995 112:707–713.
Thomson et al., "Fabrication of biodegradable polymer scaffolds to engineer trabecular bone", *J. Biomater. Sci. Polymer Edn.* 1995 7:23–38.
Yamada, H., *Strength of Biological Materials*, Wilkins & Wilkins, Baltimore, 1970.

Primary Examiner—Carlos A. Azpuru
Attorney, Agent, or Firm—Law Offices of Jane Massey Licata

[57] ABSTRACT

Methods for producing matrices useful in bone graft onlay and inlay procedures are provided. Compositions prepared by these methods are also provided.

11 Claims, No Drawings

METHODS FOR USING MICROSPHERE POLYMERS IN BONE REPLACEMENT MATRICES AND COMPOSITION PRODUCED THEREBY

This invention was made in the course of research sponsored by the National Institutes of Health. The U.S. Government may have certain rights in this invention.

INTRODUCTION

BACKGROUND OF THE INVENTION

Trauma, pathological degeneration, or congenital deformity of tissues may result in the need for surgical reconstruction or replacement. Reconstructive surgery is based upon the principle of replacing these types of defective tissues with viable, functioning alternatives. In skeletal applications, surgeons have historically used bone grafts. The two main types of bone grafts currently used are autografts and allografts. An autograft is a section of bone taken from the patient's own body, while an allograft is taken from a cadaver. This method of grafting provides the defect site with structural stability and natural osteogenic behavior. However, both types of grafts are limited by certain uncontrollable factors. For autografts, the key limitation is donor site morbidity where the remaining tissue at the harvest site is damaged by removal of the graft. Other considerations include the limited amount of bone available for harvesting, and unpredictable resorption characteristics of the graft. The main limitation of allografts has been the immunologic response to the foreign tissue of the graft. The tissue is often rejected by the body and is subject to the inflammatory response. Allografts are also capable of transmitting disease. Although a thorough screening process eliminates most of the disease carrying tissue, this method is not 100% effective.

Conventional orthopedic implants such as screws, plates, pins and rods serve as loadbearing replacements for damaged bone and are usually composed of a metal or alloy. Although these implants are capable of providing rigid fixation and stabilization of the bone, they cause improper bone remodeling of the implant site due to the large difference in the modulus between bone and metal.

These limitations have initiated the search for a dependable synthetic bone graft substitute. However, in order for an implant to be used as a replacement for bone, it must be capable of both osteointegration and osteoconduction. Osteointegration refers to direct chemical bonding of a biomaterial to the surface of bone without an intervening layer of fibrous tissue. This bonding is referred to as the implant-bone interface. A primary problem with skeletal implants is mobility. Motion of the implant not only limits its function, but also predisposes the implant site to infection and bone resorption. With a strong implant-bone interface, however, mobility is eliminated, thus allowing for proper healing to occur. Osteoconduction refers to the ability of a biomaterial to sustain cell growth and proliferation over its surface while maintaining the cellular phenotype. For osteoblasts, the phenotype includes mineralization, collagen production, and protein synthesis. Normal osteoblast function is particularly important for porous implants that require bone ingrowth for proper strength and adequate surface area for bone bonding. In addition, implants should be both biocompatible and biodegradable.

Calcium phosphate-based materials have been widely investigated for use as bone replacement materials. Most calcium phosphate biomaterials are polycrystalline ceramics characterized by a high biocompatibility, the ability to undergo osteointegration, and varying degrees of resorbability. Implants made from these materials can be in either a porous or non-porous form. Examples of commercially available calcium phosphate materials include Interpore 200® and Interpore 500®. Surgical models using porous calcium phosphate-based implant materials, however, have shown that porous implants heal more slowly than both autografts and empty defects (Nery et al. *J. Periodotol.* 1975 46:328; Levin et al. *J. Biomed. Mat. Res.* 1975 9:183). Studies on tissue ingrowth in non-resorbable implants have also shown that failure of tissue to completely fill the implant can lead to infection (Feenstra, L. and De Groot, K. "Medical use of calcium phosphate ceramics" In *Bioceramics of Calcium Phosphate*, De Groot, K. Ed., CRC Press, Boca Raton, Fla., 1983, pp 131–141; Feldman, D. and Esteridge, T. Transactions 2nd World Congress Biomaterials Society, 10th Annual Meeting, 1984, p 37.

Implants synthesized from the calcium phosphate-based material, hydroxyapatite (HA), the major mineral constituent of bone, are commercially available in a porous and non-porous form. Synthetic HA implants have excellent biocompatibility. Blocks of dense HA are not useful in reconstructive surgery because they are difficult to shape and do not permit tissue ingrowth. However, in a non-porous, particulate form, HA has been used successfully in both composite (Collagraft®) and cement (Hapset®) forms (Chow et al. *Mater. Res. Soc. Symp. Proc.* 1993 179:3–24; Cornell, C. N. *Tech. Orthop.* 1992 7:55). Due to its fragility and lack of compliance, porous HA have been largely limited to dental and maxillofacial surgery.

Tricalcium phosphate (TCP) is the other main type of calcium-phosphate based implant material. It has a biocompatibility similar to HA, but it is more resorbable than HA due to its crystal structure. The chemical structure of TCP allows it to be used as a calcium phosphate cement (CPC) (Chow, L. C. *Centen. Mem. Issue Ceramics Soc. Jpn* 1991 99:954; Mirtchi et al. *Biomaterials* 1989 10:475) which can be mixed in the operating room and thus can be easily molded to fit the implantation site. The compliance of TCP materials allow them to be used in a broader range of surgical applications than conventional ceramics.

Other types of ceramic bone replacement materials are based on silicate. The use of silicate based materials in bone replacement is associated with its biocompatibility. Unlike calcium-phosphate materials, silicate does not exist naturally in the body. However, its biocompatibility is similar to naturally occurring minerals. Examples of silicate based bone replacements include bioactive glasses.

Glass-ionomers, composite biomaterials containing both organic and inorganic components, have also been suggested for use in bone replacement.

However, a major disadvantage of many of the orthopaedic materials in current use is their lack of flexibility and inability to be custom fit to the implant site. Synthetic bone grafts come in a manufactured form that forces the surgeon to fit the surgical site around the implant. This can lead to increases in bone loss, trauma to the surrounding tissue and delayed healing time. By using an implant that can be shaped to the implant size, a customized fit can be obtained. This capability allows an implant to be used universally in all patients.

Polymers are a class of synthetic materials characterized by their high versatility. The versatility has led to the development of biodegradable, biocompatible polymers created primarily for use in medical applications. One of the most common polymers used as a biomaterial has been the polyester copolymer poly(lactic acid-glycolic acid) referred to herein as PLAGA. PLAGA is highly biocompatible, degrades into harmless monomer units and has a wide range of mechanical properties making this copolymer and its homopolymer derivatives, PLA and PGA, useful in skeletal repair and regeneration (Coombes, A. D. and Heckman, J. D. *Biomaterials* 1992 13:217–224; Mikos et al. *Polymer* 1994 35:1068–1077; Robinson et al. *Otolaryngol. Head and Neck Surg.* 1995 112:707–713; Thomson et al. *J. Biomater. Sci. Polymer Edn.* 1995 7:23–38; Devin et al. *J. Biomateri. Sci. Polymer Edn.* 1996 7:661–669).

Porous, three-dimensional matrices comprising these polymers for use in bone replacement have been prepared using various techniques. Coombes and Heckman (Biomaterials 1992 3:217–224) describe a process for preparing a microporous polymer matrix containing 50:50 PLAGA:PLA and 25:75 PLA:PLAGA. The polymer is dissolved in poor solvent with heat and the gel is formed in a mold as the polymer cools. Removal of the solvent from the matrix creates a microporous structure. However, the actual pore size of this matrix (<2 $\mu$m) is inadequate for bone ingrowth which requires a pore size falling within the range of 100–250 $\mu$m for cell growth to occur. Further, the gel cast material undergoes a significant reduction in size (5–40%) due to the removal of the solvent thus leading to problems in the production of specific shapes for clinical use. Since the amount of shrinkage varies from sample to sample, changing the mold size to compensate for the shrinkage will not result in a consistent implant size.

Robinson et al. (*Otolaryngol. Head and Neck Surg.* 1995 112:707–713) disclose a sintering technique to produce a macroporous implant wherein bulk D,L-PLA is granulated, microsieved, and sintered slightly above the glass transition temperature of PLA (58°–60° C.). Sintering causes the adjacent PLA particles to bind at their contact point producing irregularly shaped pores ranging in size from 100–300 $\mu$m. While the implants were shown to be osteoconductive in vivo, degradation of PLA caused an unexpected giant cell reaction.

Particulate leaching methods, wherein void forming particles are used to create pores in a polymer matrix have been described by Mikos et al., *Polymer* 1994 35:1068–1077 and Thomson et al., *J. Biomater. Sci. Polymer Edn* 1995 7:23–38. These methods produce highly porous, biodegradable polymer foams for use as cellular scaffolds during natural tissue replacement (Mikos et al., *Polymer* 1994 35:1068–1077; Thomson et al., *J. Biomater. Sci. Polymer Edn* 1995 7:23–38). The matrices are formed by dissolving PLA in a solvent followed by the addition of salt particles or gelatin microspheres. The composite is molded and the solvent allowed to evaporate. The resulting disks were then heated slightly beyond the $T_g$ for PLA (58°–60° C.) to ensure complete bonding of the PLA casing. Once cooled, the salt or gelatin spheres are leached out to provide a porous matrix. However, in both types of particulate leaching methods, the modulus of the matrix is significantly decreased by the high porosity. Thus, while these matrices might perform well as cellular scaffolds, in other applications such as bone replacement, their low compressive modulus would result in implant fracture and stress overloading of the newly formed bone. These problems could further lead to fractures in the surrounding bone and complete failure at the implantation site.

Laurencin et al. described a salt leaching/microsphere technique to induce pores into a 50:50 PLAGA/HA matrix (Devin et al. *J. Biomater. Sci. Polymer* Edn 1996 7:661–669). In this method, an interconnected porous network is made by the imperfect packing of polymer microspheres. The porous matrix is composed of PLAGA microspheres with particulate NaCl and HA. The particulate NaCl is used to widen the channels between the polymer microspheres. The hydroxyapatite is used to provide added support to the matrix and to allow for osteointegration. In this method, PLAGA is dissolved in a solvent to create a highly viscous solution. A 1% solution of poly(vinyl alcohol) is then added to form a water/oil (w/o) emulsion. Particulate NaCl and HA are added to the emulsion and the resulting composite mixture is molded, dried, and subjected to a salt leaching step in water. The resulting matrix is then vacuum dried, and stored in a desiccator until further use.

In vitro studies by Laurencin et al. showed osteoblast attachment and proliferation to the three-dimensional porous matrix produced by this salt leaching/microsphere method (Attawia et al., *J. Biomed. Mater. Res.* 1995 29:843–848; Attawia et al., *Biochem. and Biophys. Res. Commun.* 1995 213:639–644). Further, osteoblasts were shown to maintain their phenotype as demonstrated by the secretion of osteocalcin and alkaline phosphatase. Thus, the PLAGA/HA matrix fulfills the osteoconductive and osteointegrative requirements of a bone graft replacement. In addition, all components of the matrix are biocompatible, and the presence of ceramic HA particles allows for direct bonding to bone. However, during degradation in vitro, the mechanical strength of this matrix decreased to the lower limits of trabecular bone. Accordingly, in vivo implantation of this matrix could result in the mechanical failure of the implant or stress overloading of the newly regenerated osteoblasts.

In the present invention, a biodegradable, biocompatible polymer/ceramic composite composed of a poly(lactic acidglycolic acid) [PLAGA] and hydroxyapatite [HA] for use in three dimensional constructs for tissue engineering was prepared by three novel methods: the sintered microsphere method, the solvent casting method, and the gel microsphere method. Three-dimensional matrices produced by these methods are porous and act as cellular scaffolds during bone regeneration.

SUMMARY OF THE INVENTION

An object of the present invention is to provide methods of preparing flexible matrices composed of a biodegradable, biocompatible polymer and a calcium phosphate based material for use in three dimensional constructs for tissue engineering, and more specifically, bone replacement.

Another object of the present invention is to provide flexible bone replacement constructs prepared from these methods useful in bone graft onlay and inlay procedures.

DETAILED DESCRIPTION OF THE INVENTION

The present invention provides methods for producing a 3-dimensional porous matrix having a physical appearance and mechanical stability similar to trabecular bone. The methods use a biodegradable, biocompatible polymer and a calcium phosphate based material to create a porous structure through the packing of polymer microspheres. Examples of polymers which can be used include, but are not limited to, poly(lactic acid-glycolic acid) [PLAGA], poly(lactic acid) [PLA], poly(glycolic acid)[PGA], poly (glaxanone), poly(orthoesters), and poly(phosphazenes). Examples of calcium phosphate based materials which can be used include, but are not limited, hydroxyapatite [HA] and tricalcium phosphate [TCP].

In the methods of the present invention, polymer microspheres are first generated using a solvent evaporation technique. In this technique, the polymer is dissolved in an organic solvent and added to an aqueous solution containing a low concentration, preferably 0.5% to 5%, of surfactant. Examples of organic solvents which can be used to dissolve the polymer are well known in the art and include, but are not limited to, methylene chloride, chloroform, tetrahydrofuran, and acetone. The resulting water/organic emulsion is stirred at a constant rate to allow for the microspheres to harden by evaporation of the solvent. After the solvent has been completely evaporated, the hardened microspheres are isolated by vacuum filtration, washed, and allowed to air dry.

Using this technique, the microspheres maintain their structure and spherical shape without coalescing into larger spheres. Microsphere size can be adjusted by controlling polymer concentration, stirring speed, and surfactant concentration. Since the spheres are pre-hardened, modifications to these components results in measurable changes to matrix structure and porosity.

The accurate control over microsphere size provided by this technique correlates with a higher degree of control over pore size in the matrix. The desired pore size for a bone replacement matrix falls between 150–250 µm (Hulbert et al., *J. Biomed. Mat. Res.* 1970 4:443). Accordingly, control of the microsphere size and resulting pore size is significant to the ability of matrices to be used successfully in bone replacement procedures. Using a theoretical model based upon a simplified representation of two types of microsphere packing, optimal microsphere diameter resulting in a pore size of 150 to 250 µm was calculated to be in the range of 400 to 600 µm. The light microscopy images of the microspheres confirmed the spherical shape and smooth surface texture.

Using microspheres prepared by the solvent evaporation method, three-dimensional matrices were produced in accordance with methods of the present invention.

In one embodiment, a sintered microsphere matrix is prepared. In this method, a sintering technique is used to create a three-dimensional porous matrix composed of polymer microspheres and a calcium phosphate based material. Polymer microspheres produced by solvent evaporation are mixed with void forming particles such as NaCl, KCl, gelatin, pectin, sucrose or other sugars and the calcium phosphate based material. The mixture is then cast into a mold, compressed and sintered so that the microspheres of the casted mixture bond to each other. Sintering causes adjacent particles to bond together and is based upon the thermal transitions of a polymer. When a crystalline polymer is heated to its glass transition temperature ($T_g$), the translational, vibrational, and rotational energies of the molecule increase (Odian, G., *Principle of Polymerization*, John Wiley and Sons, New York, 1991, pp 29–33. This causes the polymer chains to become flexible and easily fold out of their packed structure. When two particles are in contact, the polymer chains at the contact point intertwine to link the particles together. The sintered mixture is demolded and cooled. As the polymer is cooled to below the glass transition temperature, the energy of the molecules decreases to near zero, and the intertwined chains pack into a crystalline structure. This results in the formation of a bond between the particles. The degree of folding between the polymer particles, which corresponds to the strength of the inter-particle bond, is dependent on the cooling rate. If the polymer is allowed to cool slowly, the degree of folding will be maximized. Void forming particles are then leached from the mixture to produce a matrix for use in bone replacement.

Sintered microsphere matrices produced by this method comprising PLAGA, HA and NaCl were cut in cross section, affixed to an scanning electron microscope (SEM) stage, and gold coated. Internal matrix structure was visualized using an Amray 1830/D4 SEM at an accelerating voltage of 20 kV. SEM pictures of the fracture surface showed that the matrix is composed of a bonded network of microspheres with a relatively consistent shape. Microsphere bonding appears to occur only at the contact points between adjacent microspheres. Random packing of the microspheres of the matrix resulted in an interconnected porous network. The interconnectivity of the matrix was complete with no indication of residual salt inclusion or dead end channels.

High magnification images (560×) of a polymer bond between two microspheres indicates complete connection between both spheres without any observable defects. The approximate length of the bond was 90 µm.

SEM images of a sintered microsphere disk were also taken from a sagittal cross section of the disk showing its thickness. The upper portion of the cross section was removed to show the fracture surface of the disk. At low magnification image (20×) the fractured surface could be seen along the top edge of the image. At this surface, microsphere structure was evident. The cross section of the spheres below the fracture surface indicated an elliptical shape and a high degree of intra-sphere bonding. The degree of bonding of the spheres was higher along the bottom edge of the image. This region had an approximate thickness of 0.6 mm. Thus, from this image, it appeared that during sintering, the weight of the Carver piston (0.92 lb.) slightly compressed the microspheres altering their shape and increasing the intra-sphere bonding. The short axis of the elliptical spheres was aligned in the direction of this compressive force.

High magnification (50×) images of the cross sectional region showed high microsphere bonding. The compressive force of the piston gave the spheres an elliptical shape thus increasing the contact point between the microspheres and the degree of bonding. Although microsphere bonding is high, the structure still remained porous. Pore size ranges from about 100–450 µm with a high interconnectivity. Inside of each pore, additional microspheres were observed. The pores are also connected along the surface thus indicating the presence of a three-dimensional porous network.

A high magnification (50×) image of the fracture surface showed microspheres ranging in size from 50–600 µm. Microsphere surface appeared rough due to the presence of NaCl particles (<75 µm) during the sintering step. Fracture of the intra-sphere bonds can be seen in the upper right corner. The area of bonding is seen as a flat plane across the microsphere surface. Examination of this region indicated that the bond between the spheres was not complete. It appears that small indentations (<33 µm) were created when the spheres were pressed together.

Cylindrical sintered matrices were fabricated using an aluminum mold resulting in samples with a length of 16 mm and a diameter of 8 mm. These dimensions correspond to the 2:1 aspect ratio needed for compressive testing. Mechanical strength of the samples was characterized as compressive modulus using an INSTRON instrument (model #1127) equipped with a Hewlett Packard Vectra 486/33U computer. Data were analyzed using Series IXµ software (INSTRON Corp.) which automatically calculated compressive modulus from stress/strain data.

Due to the shape of the sintered disk, only the cylindrical samples had dimensions suitable for compression testing.

Three sintered microsphere matrices were compression tested and resulted in an average modulus of 260.1 MPa with a standard deviation of 43.1 MPa. This value falls within the range of trabecular bone (10 MPa–2000 MPa) (Keaveney, T. M. and Hayes, W. C. "*Mechanical Properties* of Cortical and Trabecular Bone." In *Bone Volume 7: Bone Growth-B*, B. K. Hall Ed., CRC Press, Boca Raton, 1992, pp 285–344.

In another embodiment, a solvent cast microsphere matrix is prepared. In this method, polymer microspheres are mixed with void forming particles and a calcium phosphate based material. An organic solvent capable of dissolving the polymer such as methylene chloride, chloroform, tetrahydrofuran or acetone is added to the mixture in a dropwise fashion with stirring so that the polymer microspheres of the mixture aggregate. A minimal amount of solvent is used in this method to dissolve only the outer surface of the microspheres. The dissolved shell of polymer surrounding each sphere provides a means by which microsphere bonding can occur. Microspheres with a dissolved polymer shell are brought into contact with each other during the mixing step. The outer shell of one sphere becomes incorporated with the shell of other spheres. The pores between the spheres are maintained by the undissolved inner core of each microsphere. The aggregated mixture is then transferred to a mold and the mold is compressed, preferably at 5,000 to 20,000 pounds of compression for 1 to 20 minutes. The compressed, aggregated mixture is then demolded and lyophilized. As the solvent evaporates from the mixture, the dissolved polymer covering the spheres hardens creating intrasphere bonds. The porosity is maintained by the presence of the void forming particles which are then leached from the compressed aggregate to form a bone replacement matrix.

Matrix structure of a solvent cast microsphere matrix comprising PLAGA, HA and NaCl was characterized by SEM imaging. The matrix disk was cut in cross-section so that the internal structure could be visualized. The matrix section was affixed to an SEM stage, gold coated and visualized at 20 kV.

A low magnification (25×) image of the cross section of a solvent cast disk with a compositional ratio of 1:1:1 by weight [PLAGA:HA:NaCl] showed the matrix to have a fairly even distribution of pores. Microsphere structure appeared to be irregular and difficult to visualize at this magnification. However, HA particles were visible as small spheroids dispersed throughout the matrix. Pore morphology of this matrix varied from circular to oblong shapes with a range in sizes (50–250 $\mu$m) with the pores running deep into the matrix. Interconnectivity was seen by pore channels running along the cut surface.

An alternative method to the solvent evaporation technique followed by sintering or solvent casting, referred to herein as the Microsphere Gel Method, was also developed. In this method, polymer microspheres are fabricated by a modified solvent evaporation method wherein microsphere stability is maintained by controlling the amount of solvent removed. By allowing partial solvent removal, the microspheres maintain their structure while remaining in a "gel-like" form. In this form, the microspheres have a "sticky" surface that allows them to bind with one another. A calcium phosphate based material such as HA or TCP is added for matrix reinforcement. This mixture is stirred for a selected period of time and then cast into a mold and dried to form a bone replacement matrix. In this method, porosity of the matrix can be controlled by addition of a void forming particle. Preferably, however, porosity of the matrix is controlled by stirring time and microsphere size.

Matrix structure and porosity of a PLAGA:HA matrix were optimized to determine the composition and processing conditions for this method which provided the best compressive modulus. In order to determine the degree of stability needed to form a porous matrix, a modification to microsphere stirring time was conducted and varied from 1 to 2 hours: 1.00, 1.25, 1.50, 1.75, and 2.00 hours. Since the amount of solvent removed increases with stirring time, the stability of the gel microsphere also increases. The stability of the microsphere has a direct effect on matrix structure. Although highly stable microspheres will maintain their spacing and produce a structured matrix, this stability also decreases the amount and magnitude of microsphere bonding. As the stability increases, the microspheres become more visible in the matrix structure. This modification was conducted to find the optimum stirring time that would allow for significant microsphere bonding while maintaining a porous structure.

Samples fabricated from 1.75 and 2.00 hour microspheres were brittle compared to the 1.00, 1.25, and 1.50 hour samples. The 2.00 hour sample was so brittle that it could not be affixed to an SEM stage. From the results of both the SEM and stereomicroscope studies, the 1.25 hour sample was chosen as the optimum stirring time. The images from the 1.00 hour sample indicated a partial collapse of the porous network. The presence of micropores indicated that some of the solvent was trapped in the matrix and had to create its own channels during the drying steps. At times greater than 1.25 hours, the low degree of microsphere bonding resulted in porous matrices that were brittle. The stability of 1.25 hour microsphere was sufficient to allow for significant sphere bonding and moderate incorporation of HA into the polymer. The pores and HA particles were evenly distributed throughout the matrix. Pores varied through a narrow range of sizes (100–300 $\mu$m) with a relatively consistent shape. The range of pore size also encompassed the optimal size for cell ingrowth (150–250 $\mu$M). For the above reasons, the 1.25 hour stirring time was used in the fabrication of samples for the optimization studies.

Experiments to determine optimal HA and NaCl concentrations were also conducted. Since the microspheres are in a gel form, HA is not incorporated into the polymer but remains on the sphere surface and in the pores formed by microsphere spacing. In combination with NaCl, these particles influence matrix porosity and strength. In order to show that the HA particles maintained their chemical composition and were unaffected by the processing conditions, elemental analysis of the matrix was conducted. The matrix was composed of 2:1:1 PLAGA:HA:NaCl with 1.25 hour stirring. The high magnification image (169×) showed an irregular polymer surface embedded with 9 HA particles ranging in size from 40–115 $\mu$m. In order to determine the presence of HA [$Ca_{10}(PO_4)_6(OH)_2$] and any residual NaCl, the microanalyzer was set to detect the following elements: O, Na, P, Cl, and Ca. A point scan, centered on the largest HA particle, was conducted to produce an elemental spectrum showing the three largest peaks to be Ca, P, and 0 peaks. An area scan of the image was used to create elemental maps. The elemental maps for Na and Cl showed that a light coating of these ions was incorporated into the matrix. This was due to residual NaCl from the salt leaching step. The elemental map for oxygen also showed that it was dispersed throughout the matrix. This was due to the presence of oxygen in the chemical structure of both the polymer backbone and the phosphate ($PO_4$) and hydroxy (OH) groups of HA. The Ca and P maps showed localization of these elements at the HA particles. These results shows that the small spherical particles were indeed HA, and that its chemical composition was unaffected by matrix processing.

Gel microsphere matrix strength was assessed by compressive modulus on an INSTRON (model #1127) calibrated with a 20 kg weight and equipped with a Hewlett Packard Vectra 486/33U computer. Data were analyzed using INSTRON Series IX$\mu$ software which automatically calculates the modulus from the stress/strain data. All samples were machined to a 2:1 height to diameter ratio. Individual sample dimensions were measured with digital calipers and entered manually into the INSTRON computer to further accuracy. Crosshead speed was set to 1 mm/minute.

The sample with the highest modulus (1100 MPa) had a PLAGA:HA:NaCl compositional ratio of 2:2:0. The next highest sample with a modulus of 1000 MPa had a composition of 2:1:2 PLAGA:HA:NaCl. Regardless of composition, all samples had mechanical properties in the range of trabecular bone (10–2000 MPa).

The results of the compression study showed that sample with the highest modulus (1100 MPa) had a composition of 2:2:0 PLAGA:HA:NaCl. Since this sample did not have any NaCl, its porosity was completely due to the arrangement of the gel microspheres. A low magnification SEM image showed this matrix to be composed of a dense dispersion of HA particles with a moderate dispersion of pores. Microsphere structure was not apparent due the high bonding between the spheres. Two large pores were seen in the center of the sample with the remaining pores spaced throughout the matrix. The high magnification image (50×) showed pores ranging in size from 80–200 $\mu$m with a low interconnection between pores. The HA particles were heavily incorporated into the polymer except on the surface of the pore.

Incorporation of either the solvent evaporation technique in matrix fabrication by the sintering method or the solvent cast method or the modified solvent evaporation technique in the gel microsphere method significantly reduced the variance associated with microsphere stability in prior art methods. None of the samples fabricated showed any signs of cracking. When used to form a three-dimensional matrix, the prefabricated microspheres create an internal structure that remains intact and stable. With the ability to maintain microsphere structure and spacing, matrix porosity can be controlled through modifications to microsphere size, NaCl concentration and particle size.

The integrity of the porous network is dependent on the stability of the microspheres. A lack of microsphere stability leads to deterioration of the spherical packing, collapse of the porous network, and isolated inclusions of void forming particles. In both the sintering and solvent bonding methods of the present invention, the pre-hardened microspheres are mixed with the void forming particles with a diameter of <75 $\mu$m. Instead of using the particle to create the channels, which requires a larger particle size (178<X<229 $\mu$m), it is used to maintain the integrity of the voids created by the imperfect packing of the microspheres. Since the matrices have a high degree of interconnectivity and a stable porous structure, the void forming particles are completely removed by the leaching step leaving an inter-connected network of channels. This eliminates the isolated pockets of particles and dead-end channels which compromise the mechanical strength of the matrix.

The compressive yield strength of trabecular bone ranges between 40–60 MPa. The ability of matrices prepared by these methods to withstand such compression was demonstrated in porous disks cast from a Carver compression mold. Although the sintered disk was only subjected to a minimal amount of compression (0.92 lb.), a highly bonded and highly porous microsphere structure was created. Since the compression was applied during the entire sintering and cooling periods, this amount was sufficient to change the shape and degree of bonding of the microspheres. The resulting disk was extremely rigid and hard. Although the mechanical testing of the cylindrical samples only resulted in an average modulus of 260.1 MPa, the sintered disk had a much higher degree of microsphere bonding as seen by SEM analysis and was processed in a slightly different manner. Since the disk remained in the Carver mold until it reached room temperature, the disk cooled more slowly than the cylindrical samples which were immediately demolded after heating. The rate of cooling directly affects the degree of polymer chain folding. A polymer sample cooled slowly will have a higher degree of crystallinity and better mechanical properties than a sample that is cooled rapidly.

The solvent cast disk, on the other hand, was subjected to 5000 lb. (4514.5 psi/31.1 MPa) of compression during its fabrication. SEM images showed that porosity was maintained even through the sample was subjected to this high compressive force. The amount of compression during casting (31.1 MPa) almost falls with this range. The yield strength of a material is a measure of the amount of stress required to cause structural failure. Since the sample was created under 31.1 MPa of stress, the amount of stress required to cause failure of the structure will be much higher. This will lead to an increase in modulus and overall strength of the matrix.

Thus, matrices prepared by methods of the present invention are clearly useful in bone graft onlay procedures of trabecular bone. Further, matrices prepared by these methods can be made temporarily flexible. The induced flexibility is based upon the thermal transition of the main component of the matrix, the biodegradable, biocompatible polymer. The glass transition temperature ($T_g$) of a polymer is the point at which the chains of the polymer become flexible. For example, a rigid form fitting onlay comprising PLAGA can be made flexible by heating the implant past 57.4° C., the $T_g$ for this polymer. As the temperature of the implant increase past the $T_g$, the implant becomes more and more flexible. After a few seconds, the implant is ready to be molded to fit the surgical site. With this flexibility, the implant can be placed over, for example, a fractured bone, and contoured to fit the bone surface. As the implant cools, it becomes rigid again but maintains the shape of the surgical or onlay site. Once the implant completely hardens, the onlay will reinforce the surrounding bone in a custom fit and provide a scaffold for bony fusion.

In addition, it is believed that samples fabricated using the solvent cast method of the present invention have sufficient strength to be useful in cortical bone replacement (Modulus 17 MPa, Compressive Strength 150–160 MPa) (Yamada, H. *Strength of Biological Materials*, Wilkins & Wilkins, Baltimore, 1970).

Matrices produced by these methods can also be used in bone graft inlay procedures. Bone graft inlays require a somewhat different design criteria. This type of graft is placed in bone to reinforce a defect or replace missing or diseased bone. Thus, in one embodiment, a rigid matrix prepared by a method of the present invention can be specifically molded to fit the defective or missing area of the bone.

Alternatively, the implant material can be of a moldable, putty form that will eventually harden and be able to withstand normal physiological stresses. Because the material is in putty form, implants of this nature are usually non-porous. Conventional materials of this type have been characterized as bone cements. Although bone cements are in a self-setting putty form and have the required mechanical properties, they are not resorbable and eventually fail after prolonged implantation. By using biodegradable materials, the implant can provide a temporary site for bone regeneration and avoid problems associated with prolonged implantation.

Calcium sulfate hemihydrate (plaster of Paris) has been used in the past to fill bone defects. This is a degradable material that, when mixed with water, forms a moldable putty which eventually hardens into a rigid form. However, the use of calcium sulfate ($CaSO_4$) implants has been limited due to the relatively fast resorption of the material. The degradation time of $CaSO_4$ (usually 2–4 weeks) does not allow for the complete formation of bone. After a $CaSO_4$ implant degrades, it is usually replaced by a combination of fibrous and osseus tissues. This combination of tissues is not capable of fully supporting the defect site.

In the present invention, a matrix comprising a biodegradable, biocompatible polymer microsphere coated with a calcium phosphate based material encased in $CaSO_4$ is provided. Coated microspheres are derived from the gel microsphere method. In this method, the microspheres are stirred for a set time to produce the desired structure as described above. When mixed with particles of a calcium phosphate based material such as HA or TCP, these gel spheres form a three-dimensional porous composite. As the stability of the spheres increases, the particles become less incorporated into the polymer and begin to coat the gel microspheres. Coating of the microspheres with the calcium phosphate based particles occurs when the stability is increased to the point where intrasphere bonding is almost completely eliminated. For example, to produce HA coated PLAGA microspheres, a significant decrease in intrasphere bonding occurs when the stirring time is greater than 1:30 hours and the stirring speed is 250 to 350 RPM. At these conditions, PLAGA microspheres coated with small HA particles are formed.

When the coated microspheres are mixed with calcium sulfate hemihydrate and water, a moldable composite is produced. In a preferred embodiment, calcium sulfate hemihydrate is combined with HA coated PLAGA microspheres at a 2:1 w/w ratio and mixed. Distilled water is then added and the composite mixed to first form a paste-like substance which then changes into a moldable composite dough. At this point, the composition is ready to be shaped to the implant site. Once molded to the desired shape, the composite dough sets via the conversion of calcium sulfate hemihydrate to calcium sulfate. As this reaction proceeds, the moldable dough hardens into a final implant form.

Incorporation of the coated microspheres into the matrix, provides the composition of the instant invention with advantages over conventional $CaSO_4$ implants. The coated microspheres permit the implant to be resorbed through a step-wise degradation. Upon initial implantation, the $CaSO_4$ component begins to degrade. After approximately two weeks, the $CaSO_4$ material is replaced by fibro-osseous tissue. Unlike pure $CaSO_4$ implants, however, this tissue is reinforced with coated microspheres thus providing the implant site with additional strength during bone formation. The next step in the degradation occurs as the fibrous tissue is converted to bone. During this time, the polymer microspheres begin to degrade. Although this reduces the reinforcing effect of the particles, the implant is stabilized by the newly forming bone. Following the complete resorption of both the $CaSO_4$ and polymer components, the calcium phosphate based particles are then resorbed.

This step-wise degradation of the matrix of the present invention provides the implant site with decreasing reinforcement which allows for the gradual loading of the newly formed bone. Since bone is a dynamic tissue that responds to changes in stress, gradual loading of the regenerating bone stimulates further bone formation without causing stress damage to the new osteoblasts. Thus, the moldable composite of the present invention enables the implant to be multifunctional. Not only can this material be molded to precisely fit a defect site, it temporarily serves as a template for new bone generation, a reinforcing agent and a scaffold for new bone growth.

The following nonlimiting examples are provided to further illustrate the instant invention.

EXAMPLES

Example 1

Solvent Evaporation Technique

PLAGA was dissolved in methylene chloride in a 1:5 w/v ratio. A 1% solution of PVA (250 ml) was used as a surfactant. The PLAGA solution is added drop-wise to the PVA solution with stirring. The PLAGA/PVA emulsion was stirred at a constant rate for 10 hours using a magnetic stirrer set at the lowest setting. This allowed for complete evaporation of the solvent. The microspheres were isolated by vacuum filtration, washed with de-ionized water and allowed to dry overnight. The dry microspheres were lightly ground with a mortar and pestle to break up any clumps. The free flowing microspheres were then sieved into the following size ranges: >590 µm, 297<X<590 µm, 229<X<297 µm, 178<X<229 µm, 152<X<178 µm, 117<X<152 µm, <117 µm.

Example 2

Preparation of Sintered Matrix

Pre-fabricated microspheres with a diameter of 178<X<229 µm and NaCl (particle size <75 µm) were thoroughly mixed in a 5:1 PLAGA:NaCl ratio. The mixture was cast into an aluminum mold which was then compressed and heated to 79° C. heated for 3 hours. This temperature was above the glass transition temperature of PLAGA (57.4° C.) and allowed a suitable microsphere bond to develop. After 3 hours, the sample was demolded and slowly cooled to room temperature. The sample was then placed in a water bath for 4 hours. Due to the high degree of interconnectivity of the sintered matrix, the length of the salt leaching step was decreased significantly to reduce polymer degradation in the water bath. After the salt leaching process, the sample was vacuum dried for 48 hours. Matrices prepared without any NaCl were not subjected to the salt leaching process.

Example 3

Preparation of Compression Molded Matrix

In a glass vial, 2.4525 g of PLAGA microspheres with a size range of 178<X<298 µm were combined with 0.4930 g of NaCl (<75 µm). The polymer/salt mixture was thoroughly mixed and poured into a Carver compression mold. The only compressive force that the sample was subjected to was from the weight of the Carver mold's piston (0.92 lb.). The entire mold containing the microsphere/salt mixture was placed in an oven and heated at 75° C. for 1 hour. The mold was then removed from the oven and allowed to slowly cool to room temperature over a period of 24 hours. Following this cooling period, the sample was demolded and placed in a water bath for 24 hours in order to leach out the NaCl particles. The sample was then placed in a vacuum for 24 hours until completely dry. The use of the Carver compression mold resulted in a microsphere disk with a diameter of 2.8 cm and a thickness of 0.4 cm.

Example 4

Preparation of Solvent Cast Matrix

In a glass vial, 0.7815 g of pre-fabricated PLAGA microspheres (117<X<229 μm) was mixed with 0.7881 g of NaCl (178<X<229 μm) and 0.7817 g of HA to give a 1:1:1 compositional ratio of PLAGA:HA:NaCl. Methylene chloride was added dropwise to the mixture. The addition of each drop caused aggregation of the mixture in the area where it made contact. The mixture was stirred after the addition of each drop. After 0.5 ml of solvent had been added, the mixture had a solid consistency, and was transferred to a Carver mold. The mold was compressed at 5000 pounds for 1 minute. Due to the low amount of solvent, the sample was immediately demolded and placed in the lyophilizer for 24 hours. Once dry, the sample was placed in a water bath for 48 hours. The salt was removed, and the sample was dried in a vacuum for an additional 48 hours.

Example 5

Preparation of Gel Microsphere Matrix

In a 600 ml beaker, 2.0 g of PLAGA (58:42) was dissolved in 10 ml of methylene chloride to form a 1:5 w/v polymer solution. The polymer solution was poured into 300 ml of a 1% PVA solution with stirring. The resulting emulsion was stirred for 1.25 hours. Once stirring was complete, the microspheres were allowed to settle to the bottom of the beaker. A portion of the PVA solution was suctioned off leaving a residual amount to aid in transfer. The microspheres were transferred to a conical tube aided by the excess PVA solution and the remaining PVA solution from the transfer was brought down to the level of the microspheres. At this point, weighed amounts of NaCl and HA were added. The mixture was thoroughly stirred and then cast into a 20×8 mm cylindrical mold. The sample was allowed to air dry for 24 hours. The matrix was demolded and placed into a lyophilizer for an additional 48 hours. Once completely dry, the sample was placed in a water bath for 48 hours for the salt leaching process. If the sample was fabricated without the use of NaCl, then this step was omitted. The water was changed after 24 hours. The sample was removed from the water bath and placed in the lyophilizer for 48 hours. The dried matrix was sealed in a glass vial for later use.

Example 6

SEM Analysis of matrices

Cylindrical samples of the matrices were cut in cross-section into thin disks (8 mm diameter/2 mm thickness) which were affixed to an SEM stage. Samples were gold coated with a Denton Desk-1 sputter coater. Sample morphology was viewed on an Amray 1340/D4 SEM at an accelerating voltage of 20 kV. Elemental analysis was conducted using a Link Isis energy dispersive microanalyzer at an accelerating voltage of 20 kV.

Example 7

Surface morphology of matrices

Surface morphology of the matrices was examined with a AO Spencer Stereomicroscope at a magnification of 20x. After the drying process was completed, samples of matrices were placed in a glass evaporation dish, and positioned directly on the microscope stage.

Example 8

Determination of mechanical strength of matrices

Sample of the matrices were machined to have a 2:1 height:diameter aspect ratio. Mechanical strength of the samples was characterized using an INSTRON model 1127 equipped with a Hewlett Packard Vectra 486/33U computer. Data were analyzed using Series IX software (INSTRON Corp.) which automatically calculated compressive modulus from stress/strain data.

What is claimed is:

1. A method of producing a bone replacement matrix comprising:
   (a) generating biodegradable, biocompatible polymer microspheres by solvent evaporation;
   (b) mixing the biodegradable, biocompatible polymer microspheres with a void forming particle and a calcium phosphate based material;
   (c) casting the mixture into a mold and compressing the mold to form a casted mixture;
   (d) sintering the casted mixture so that the polymer microspheres bond to each other;
   (e) demolding and cooling the sintered mixture; and
   (f) leaching the void forming particles from the sintered mixture to form a bone replacement matrix.

2. The method of claim 1 further comprising heating the bone replacement matrix formed in step (f) above the glass transition temperature of the biodegradable, biocompatible, polymer microspheres so that the bone replacement matrix is flexible.

3. A composition for use in bone replacement produced by the method of claim 1.

4. A method of producing a bone replacement matrix comprising:
   (a) generating biodegradable, biocompatible polymer microspheres by solvent evaporation;
   (b) mixing the biodegradable, biocompatible microspheres with a void forming particle and a calcium phosphate based material;
   (c) adding solvent to the mixture in a dropwise fashion with stirring so that the polymer microspheres of the mixture aggregate;
   (d) transferring the aggregated microspheres to a mold and compressing the mold;
   (e) demolding and lyophilizing the molded microspheres; and
   (f) leaching the void forming particles from the molded microspheres to form a bone replacement matrix.

5. The method of claim 4 further comprising heating the bone replacement matrix formed in step (f) above the glass transition temperature of the biodegradable, biocompatible, polymer microspheres so that the bone replacement matrix is flexible.

6. A composition for use in a bone replacement procedure produced by the method of claim 4.

7. A method of producing a bone replacement matrix comprising:
   (a) generating gel-like polymer microspheres by a modified solvent evaporation technique;
   (b) adding a calcium phosphate based material to the gel-like polymer microspheres to form a mixture;

(c) stirring the mixture; and (d) casting the mixture into a mold and drying the molded mixture to form a bone replacement matrix.

8. The method of claim 7 further comprising heating the bone replacement matrix formed in step (d) above the glass transition temperature of the biodegradable, biocompatible, polymer microspheres so that the bone replacement matrix is flexible.

9. A composition for use as a bone replacement matrix produced by the method of claim 7.

10. A method for producing a bone replacement matrix useful in bone graft inlay procedures comprising:

(a) generating polymer microspheres coated with a calcium phosphate based material;

(b) mixing the coated polymer microspheres with calcium sulfate hemihydrate and water to produce a moldable composite;

(c) molding the composite into a shape to fit a site for the bone graft inlay; and (d) drying the shaped composite to hardness to produce a bone replacement construct for insert into the bone graft inlay site.

11. A composition for use as a bone replacement construct in bone inlay procedures produced by the method of claim 10.

* * * * *

UNITED STATES PATENT AND TRADEMARK OFFICE
CERTIFICATE OF CORRECTION

PATENT NO. : 5,866,155
DATED : February 2, 1999
INVENTOR(S) : Laurencin et al.

It is certified that error appears in the above-identified patent and that said Letters Patent is hereby corrected as shown below:

On the title page, item[54] and Col.1 line 3:

--METHODS FOR USING MICROSPHERE POLYMERS IN BONE REPLACEMENT MATRICES AND COMPOSITIONS PRODUCED THEREBY--.

At col 3 line 16, please delete "3:217-224" and insert therefor --13:217-224--.

Signed and Sealed this

Twenty-ninth Day of June, 1999

Attest:

Q. TODD DICKINSON

Attesting Officer

Acting Commissioner of Patents and Trademarks